US012788955B2

(12) United States Patent
Espinosa et al.

(10) Patent No.: US 12,788,955 B2
(45) Date of Patent: Nov. 10, 2026

(54) ELECTRICAL DISCONNECT FOR TATTOO MACHINE

(71) Applicant: FK Irons Inc., Doral, FL (US)

(72) Inventors: Roberto Hernandez Espinosa, Pembroke Pines, FL (US); Helber Ivan Tovar, Hialeah Gardens, FL (US); Gaston Alfonso Siciliano, Bal Harbour, FL (US)

(73) Assignee: FK Irons Inc., Doral, FL (US)

( * ) Notice: Subject to any disclaimer, the term of this patent is extended or adjusted under 35 U.S.C. 154(b) by 38 days.

(21) Appl. No.: 18/963,906

(22) Filed: Nov. 29, 2024

(65) Prior Publication Data

US 2025/0177713 A1 Jun. 5, 2025

Related U.S. Application Data

(60) Provisional application No. 63/605,342, filed on Dec. 1, 2023.

(51) Int. Cl.
*A61M 37/00* (2006.01)

(52) U.S. Cl.
CPC . *A61M 37/0076* (2013.01); *A61M 2205/8206* (2013.01)

(58) Field of Classification Search
None
See application file for complete search history.

(56) References Cited

U.S. PATENT DOCUMENTS 8,238,086 B2 8/2012 Ou
8,460,813 B2 6/2013 Lerner et al.
9,398,637 B2 7/2016 Montevirgen et al.
10,471,246 B1 * 11/2019 Lipscomb ......... A61M 37/0076
2005/0277973 A1 * 12/2005 Huang .............. A61M 37/0076 606/185
2008/0077170 A1 * 3/2008 Kluge .................. A01K 11/005 606/186

(Continued)

FOREIGN PATENT DOCUMENTS

KR 102078651 B1 2/2020
WO 2021191479 A1 9/2021

OTHER PUBLICATIONS

International Search Report and Written Opinion received for PCT Patent Application No. PCT/ES2021/070124, mailed on Sep. 30, 2021, 19 pages.

*Primary Examiner* — Shaun L David

(74) *Attorney, Agent, or Firm* — Akerman LLP; Peter A. Chiabotti

(57) ABSTRACT

A tattoo machine with a three-way electrical disconnect is disclosed. The tattoo machine includes a tattoo machine housing, which further includes a grip section that houses a motor and a battery housing that houses a battery that powers the motor. The battery housing section has a detachable locking cap, which houses a contact plate. The tattoo machine also includes an electrical contact housed within a distal portion of the battery housing that engages with the contact plate in the locking cap when the locking cap is attached to the battery housing. The tattoo machine is turned on by rotating the locking cap in a clockwise direction and turned off by rotating the locking cap in a counter-clockwise direction.

19 Claims, 6 Drawing Sheets

(56) References Cited

U.S. PATENT DOCUMENTS

| | | | | |
|---|---|---|---|---|
| 2008/0300615 | A1* | 12/2008 | Colton | A61M 37/0076<br>606/186 |
| 2010/0241151 | A1* | 9/2010 | Rickard | A61M 37/0076<br>606/186 |
| 2011/0288575 | A1* | 11/2011 | Colton | A61M 37/0076<br>606/185 |
| 2016/0121093 | A1* | 5/2016 | Fan | H04W 4/80<br>606/185 |
| 2017/0021154 | A1* | 1/2017 | Johansson | A61M 37/0076 |
| 2018/0369553 | A1* | 12/2018 | Siciliano | A61B 17/3476 |
| 2020/0306519 | A1* | 10/2020 | Smead | A61M 37/0076 |
| 2021/0213370 | A1* | 7/2021 | Wang | A63H 33/26 |
| 2021/0244928 | A1* | 8/2021 | Siciliano | A61M 37/0076 |
| 2021/0322747 | A1* | 10/2021 | Grassano | A61M 37/0076 |
| 2021/0402162 | A1* | 12/2021 | Siciliano | A61M 37/0076 |
| 2022/0015251 | A1* | 1/2022 | Grassano | A61M 37/0076 |
| 2022/0161012 | A1* | 5/2022 | Chen | A61M 37/0076 |
| 2023/0040685 | A1* | 2/2023 | Xiao | A61M 37/0076 |
| 2023/0201552 | A1* | 6/2023 | Grassano | A61M 37/0076<br>81/9.22 |

* cited by examiner

ELECTRICAL DISCONNECT FOR TATTOO MACHINE

CROSS REFERENCE TO RELATED APPLICATIONS

This application claims the priority benefit of Provisional Application No. 63/605,342 filed on Dec. 1, 2023, which is incorporated by reference in its entirety.

FIELD OF THE APPLICATION

The present application relates to tattoo, permanent makeup and micropigmentation machines.

BACKGROUND

Tattoo machines, commonly referred to as tattoo pens, are used to apply tattoo ink, permanent makeup and pigments to a person's body and skin. A tattoo pen body is typically cylindrically shaped for ease of the tattoo artist's grip and comfort when tattooing a customer. Tattoo pens with batteries allow for a user to freely orientate the tattoo pen for the best orientation for drawing on what can be uneven surfaces. Tattoo pens can have removable batteries. The tattoo pen provides an artist with optimal functionality and comfort when applying tattoos. Such functionality includes being free to tattoo customers both inside a traditional studio and other locations.

SUMMARY

The tattoo machine comprises a tattoo machine housing, a contact plate with a plurality of protrusions that extend radially relative to a longitudinal axis defined by tattoo machine housing, and an electrical contact housed within a distal portion of an interior of the tattoo machine housing. The tattoo machine housing comprises a grip section that houses a motor and a battery housing that houses a battery that powers the motor. The battery housing section has a detachable locking cap, where the battery housing section detachably couples with the locking cap.

In an embodiment of the tattoo machine, the tattoo machine is turned on by rotating the locking cap in a clockwise direction. In the same embodiment, the tattoo machine is turned off by rotating the locking cap in a counter-clockwise direction.

In an embodiment of the tattoo machine, the locking cap further comprises a proximal first ring, a middle second ring, and a distal convex portion. The proximal first ring is fixedly attached to a proximal side of the middle second ring and the middle second ring is fixedly attached to a proximal side of the distal convex portion. The outer diameter of the middle second ring is larger than an outer diameter of the proximal first ring. The distal convex cap includes recesses and a flat surface located on a distal side of the distal convex portion.

In an embodiment of the tattoo machine, the distal end of the battery housing section further includes an interior space for receiving the proximal first ring of the locking cap. The proximal first ring includes tabs on an exterior radial surface. The tabs are received by notches in the interior space on the distal end of the battery housing section. The locking cap is secured to the battery housing section by placing the tabs of the proximal first ring within the notches on the distal end of the battery housing section and rotating the locking cap in either a first direction or second direction, such as clockwise or counterclockwise. The interior space further includes stops located a distance from the notches, wherein the tabs abut against the stops when the locking cap is rotated in either direction.

In an embodiment of the tattoo machine, the plurality of protrusions are located on a peripheral edge of the contact plate. The plurality of protrusions engage with indentations located on an inner circumferential edge of a interior space on the proximal end of the locking cap to detachably secure the contact plate to the locking cap.

In an embodiment of the tattoo machine, the contact plate includes contact areas and non-contact areas. The electrical contact makes contact with the contact area of the contact plate when the locking cap is rotated in a first direction. Power is generated between the battery and the motor when the electrical contact makes contact with the contact area of the contact plate.

In the same embodiment of the tattoo machine, the electrical contact makes contact with the non-contact area of the contact plate when the locking cap is rotated in a second direction. The battery and the motor are maintained in an electrically disconnected state when the electrical contact makes contact with the non-contact area of the contact plate. The contact areas and non-contact areas are oriented with respect to the protrusions such that the contact plate can be placed within the locking cap in any configuration.

DESCRIPTION OF DRAWINGS

For a more complete understanding of the present disclosure and its features and advantages, reference is now made to the following description, taken in conjunction with the accompanying drawings, in which.

DETAILED DESCRIPTION

Tattoo Machine

Figure 1:
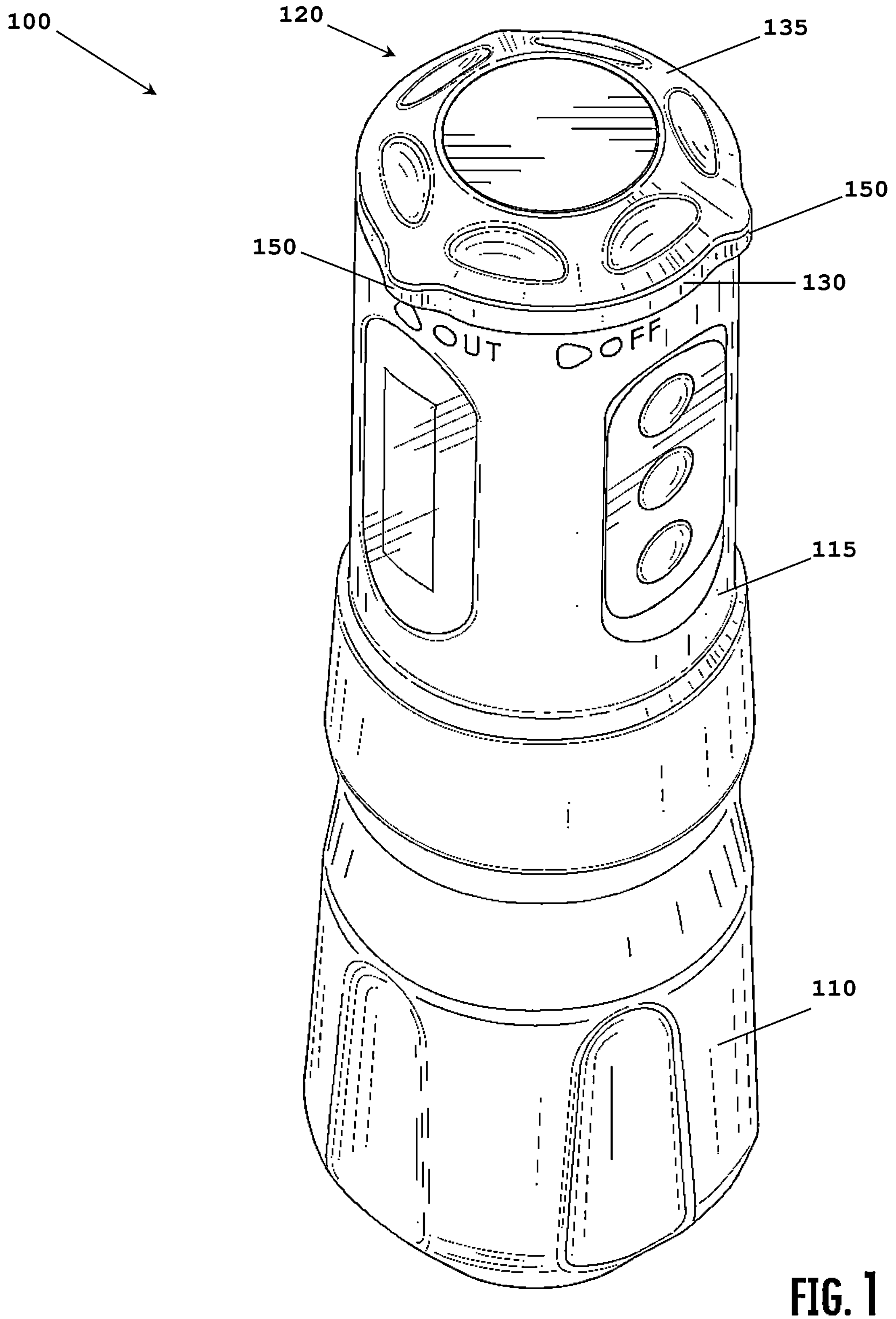
FIG. 1 is a perspective view of the tattoo machine.
Figure 2:
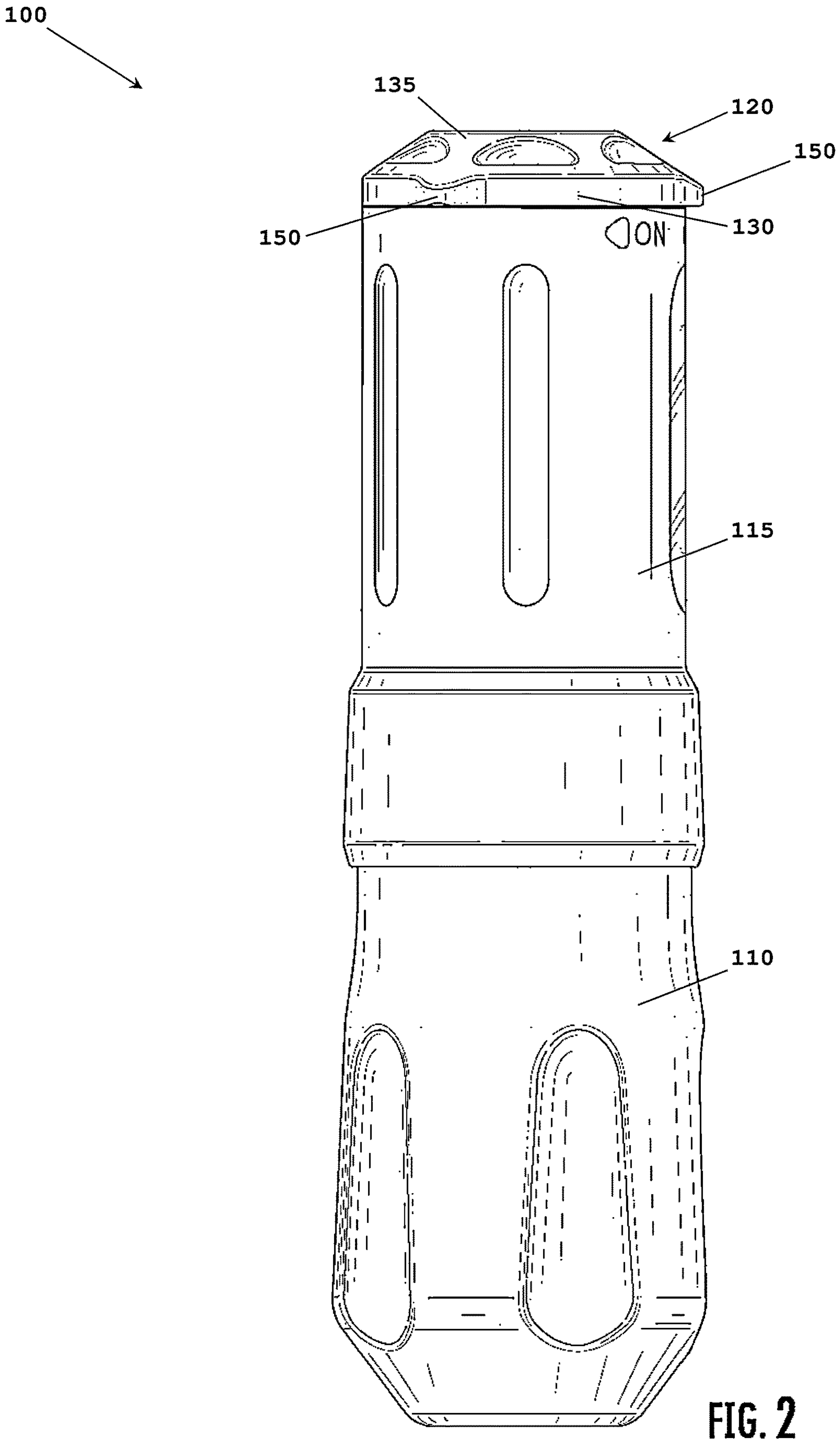
FIG. 2 is a side view of the tattoo machine.

FIGS. 1 and 2 illustrate a tattoo machine 100 according to some embodiments. The tattoo machine can include a permanent makeup machine, a micropigmentation machine and/or a needling machine. The tattoo machine 100 may include a cylindrical housing 105, a motor, display, buttons, and a battery. The cylindrical housing 105 may include a grip section 110 at the work end where a needle applies ink, a battery housing 115, and a battery locking cap 120 opposite the work end. The motor may be housed within the interior of the grip section 110. The battery may be housed within a portion of the interior of the battery housing 115. In some embodiments, the battery housing 115 may detachably couple to the distal end of the grip section 110 via a threaded attachment or magnetic coupling. The proximal end of locking cap 120 may detachably couple to the distal end of the battery housing 115.

Locking Cap

Figure 3:
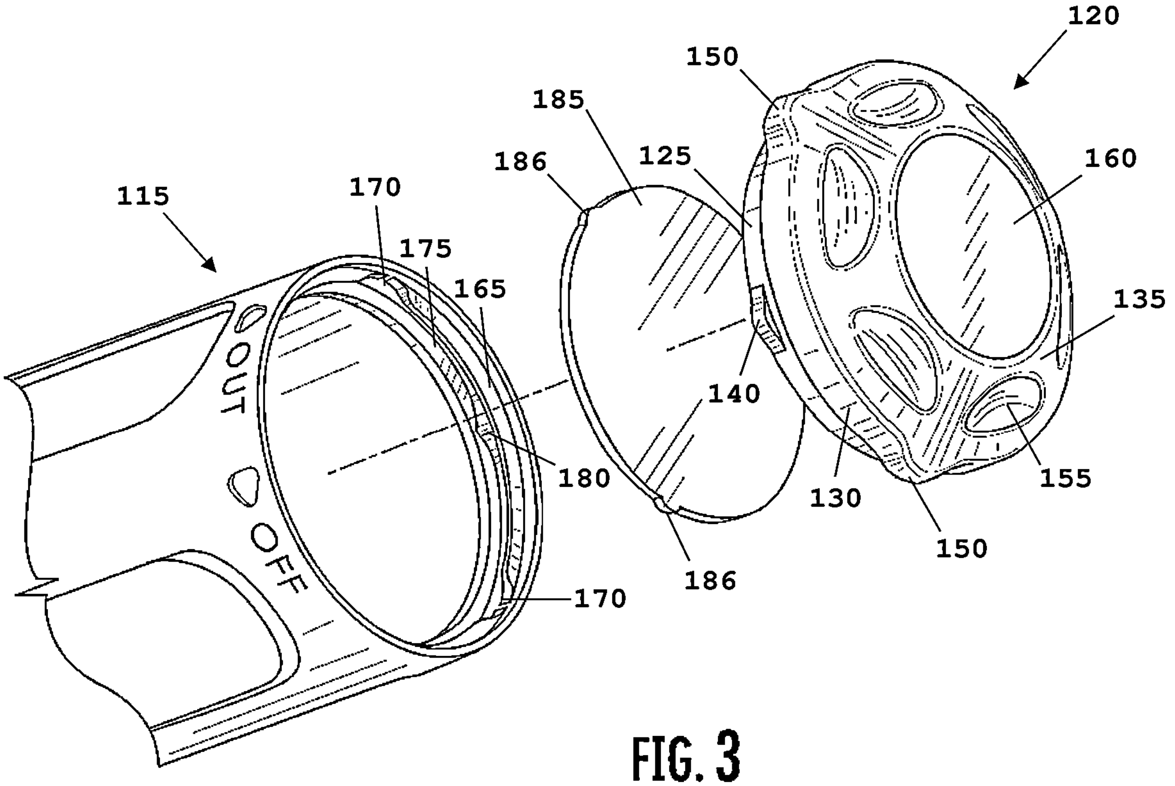
FIG. 3 is an exploded view of the distal end of the tattoo machine.
Figure 4:
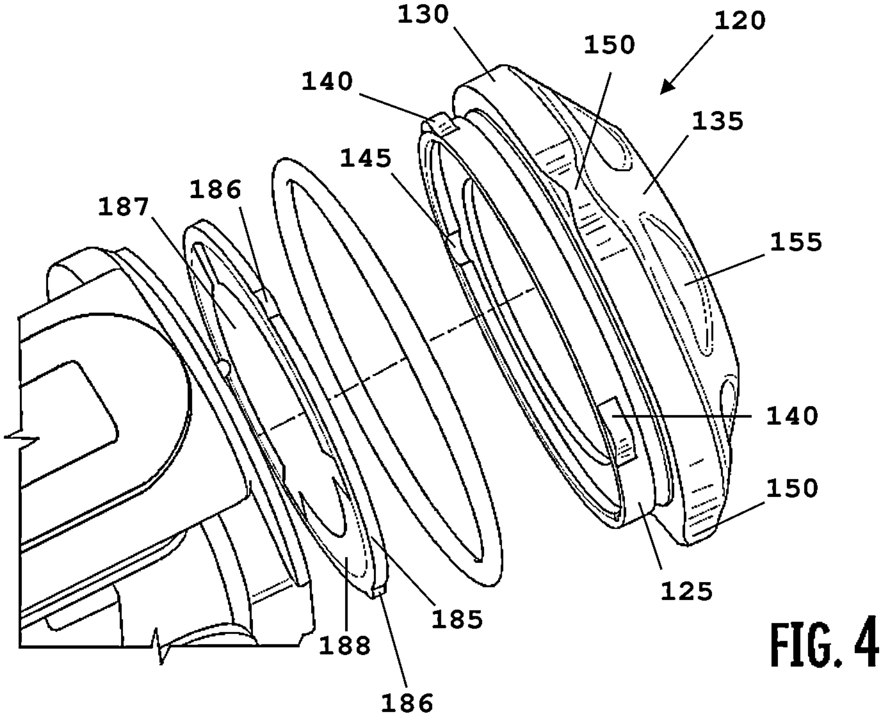
FIG. 4 is a perspective exploded view of the distal end of the tattoo machine.

FIGS. 3 and 4 illustrate an exploded view of the distal end of tattoo machine 100. The locking cap 115 may include a proximal first ring 125, a middle second ring 130, and distal convex portion 135. The proximal first ring 125, the middle second ring 130, and the distal convex portion 135 may be integral with each other.

The proximal first ring 125 may have tabs 140 positioned on the exterior radial surface of the proximal first ring 125 and integral with the proximal first ring 125 and the locking cap 120. The tabs 140 may extend radially outward from a longitudinal central axis of the tattoo machine 100. In some embodiments, tabs 140 may be positioned approximately 120° off set from an adjacent tab 140. The proximal first ring 125 may also have an interior space on the proximal end of the proximal first ring 125. The interior space may have indentations 145 on the inner wall of the interior space. The proximal first ring 125 may also include a groove positioned on a distal end of proximal first ring 125. The groove receives an O-ring, which provides a water-tight seal between the distal end of battery housing 115 and locking cap 120.

The middle second ring 130 may have a larger outer diameter than the proximal first ring 125. The middle second ring 130 may have projections 150 positioned on the exterior radial surface of the middle second ring 130 and integral with the middle second ring 130 and the locking cap 120. The projections 150 may extend radially outward from a longitudinal central axis of the tattoo machine 100. The projections 150 may extend beyond the exterior surface of the battery housing 115 a length that is 2% greater than the circumference of the outer surface of the battery housing 115. Other arrangements are projections 150 extending beyond the exterior surface of the battery housing 115 by 1%-10% greater than the circumference of the outer surface of the battery housing 115. In another arrangement, the projections 150 may extend, 0.3 cm to 1.5 cm beyond the circumference of the outer surface of the battery housing 115. In some arrangements, the projections 150 may extend a uniform distance. In other arrangement, the projections 150 may extend non-uniform distances. In arrangements, each projection 150 can be located circumferentially on cap 120 a distance from a tab 140 such that rotating the locking cap 120 via projection 150 a quarter turn secures the locking cap 120 to the tattoo machine 100.

The distal convex portion 135 may include concentrically arranged recesses 155 and a flat surface 160. A user may use recesses 155 to rotate locking cap 120 by placing their fingertips within the recesses 155 and rotating the locking cap 120 in either a first direction, such as clockwise direction, or a second direction, such as a counter-clockwise direction.

The locking cap 120 may be made from plastic, metal, rubber, or a combination thereof. In one embodiment, the locking cap 120 may be formed from a thermoplastic material using an injection molding process. In another embodiment, the locking cap 120 may be formed from metal using a mill, lathe, or water jet cutting machine or other process to form tabs 140 and protrusions 186 that are integrated with locking cap 120. In some embodiments, the outer surface of the locking cap 120 may be treated to provide additional grip to a user rotating the locking cap 120. For example, the entire exterior surface of the locking cap 120 may be rubberized. In another example, the projections 150 may be textured using patterns such as knurling or cross-hatching.

Battery Housing

FIGS. 1 and 2 illustrate an exterior surface of battery housing 115 according to an embodiment of the tattoo machine. The exterior surface of battery housing 115 may have cut-outs for carrying the display and buttons. The cut-outs may be located in a middle portion of the exterior of the battery housing 115. The distal end of the battery housing 115 may have the words "ON", "OFF", and "OUT", along with arrows corresponding to directions for rotating the locking cap 120, etched or engraved into the exterior surface of the battery housing 115.

Figure 5:
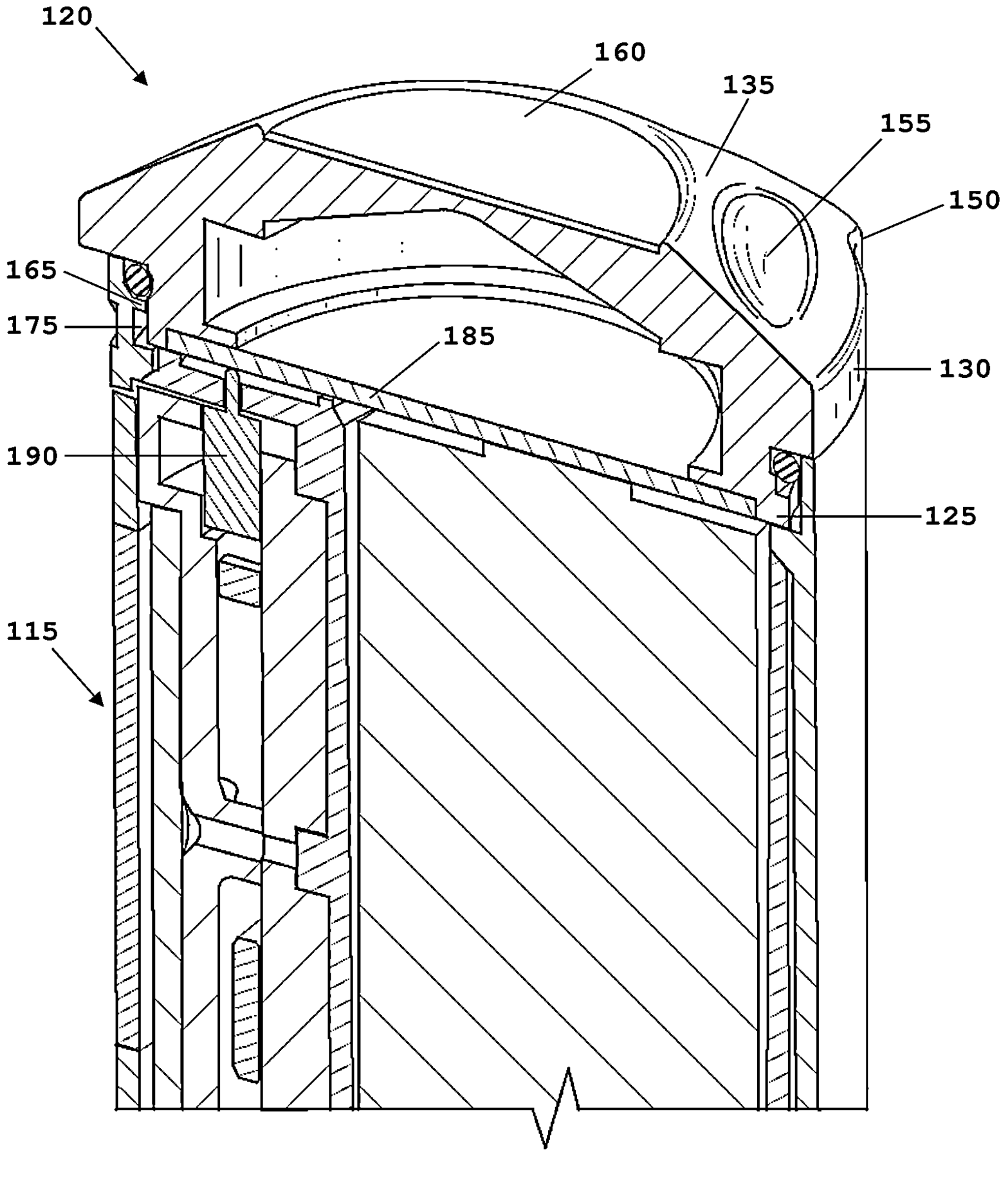
FIG. 5 is a sagittal cross-sectional view of the distal end of the tattoo machine.

FIGS. 3-5 illustrate an interior space at the distal end of battery housing 115. The interior space may have a circumferential lip 165 positioned on an inner wall of the interior space. The circumferential lip 165 may have notches 170 for receiving tabs 140 when the proximal first ring 125 of the locking cap 120 is placed inside the interior space. In some embodiments, notches 170 are positioned approximately 120° off set from an adjacent notch 170. The circumferential lip 165 may be positioned a distance from the back wall of the interior space to create a channel 175 underneath the circumferential lip 165. In some embodiments, the circumferential lip 165 is positioned between approximately 0.1 cm and 0.3 cm from the back wall of the interior space. The channel 175 beneath the circumferential lip 165 may have stops 180, which abut against tabs 140 when locking cap 120 is rotated in either a clockwise or counter-clockwise direction. In some embodiments, the stops 180 may be positioned approximately 180° off set from an adjacent stop 180.

The locking cap 120 may be detachably secured to the battery housing 115 by placing the proximal first ring 125 of locking cap 120 into the interior space at the distal end of the battery housing 115 and rotating the locking cap 120 in either a clockwise or counter-clockwise direction. When the proximal first ring 125 of locking cap 120 is placed into the interior space at the distal end of the battery housing 115, the tabs 140 on the exterior surface of proximal first ring 125 pass through the notches 170 on the circumferential lip 165 and come to a resting point within the channel 175 beneath the circumferential lip 165. The tabs 140 and notches 170 may be oriented with respect to each other such that locking cap 120 cannot be attached to the battery housing 115 unless each tab 140 is aligned with each of the corresponding notches 170. Once the tabs 140 are properly aligned with notches 170 and the tabs 140 are sitting within the channel 175, a user may rotate locking cap 120 in either a clockwise or counter-clockwise direction to secure the locking cap 120 to the battery housing 115.

Contact Plate

FIGS. 3-8 illustrate a contact plate 185 according to an embodiment of the tattoo machine. The contact plate 185 may be a circular shape and may have an outer circumference that is approximately equal to the inner circumference of the interior space at the proximal end of the proximal first ring 125. The contact plate 185 may include a plurality of protrusions 186 on an outer peripheral edge of the contact plate 185. The protrusions 186 may extend radially outward from a longitudinal central axis of the tattoo machine 100. In some embodiments, the contact plate 185 is detachably secured within an interior space on the proximal end of the proximal first ring 125 of the locking cap 120. The contact plate 185 may be detachably secured to the locking cap 120 by aligning and placing the protrusions 186 of the contact plate 185 within the corresponding indentations 145 on the inner wall of the interior space of the proximal first ring 125. The friction between the protrusions 186 and indentations 145 detachably secure the contact plate 185 within the interior space at the proximal end of the proximal first ring 125.

The contact plate 185 may have contact areas 187 and non-contact areas 188. The contact areas 187 may be made out of copper or other electrically conductive material. The non-contact areas 188 may be made out of a photo-resistive material or other electrically resistive material. The contact areas 187 and non-contact areas 188 may be oriented with respect to the protrusions 186 such that the contact plate 185 can be placed within the locking cap 120 in any configuration. Alternatively, a single contact area 187 can be provided where a predetermined arrangement is employed for securing the locking cap 120 to the battery housing 115. The contact areas 187 can be formed equidistant from each adjacent contact area 187 such that rotating the locking cap 120 in either direction a uniform distance either turns the tattoo machine on or off by connection or disconnection the tattoo machine. In another arrangement, the contact areas 187 can arranged non-uniform distances from each other. With such arrangements, a longer or greater rotation of the locking cap 187 may be required to complete the electrical connection and/or a shorter or lessor rotation of the locking cap 187 may be required to complete the electrical connection. In such an arrangement, the amount of rotation required to turn off a machine will be different than the amount of rotation required to turn on the machine. The contact plate 185 may be fabricated using the same process that is used to fabricate printed circuit boards.

Electric Pin/PCB

Figure 6:
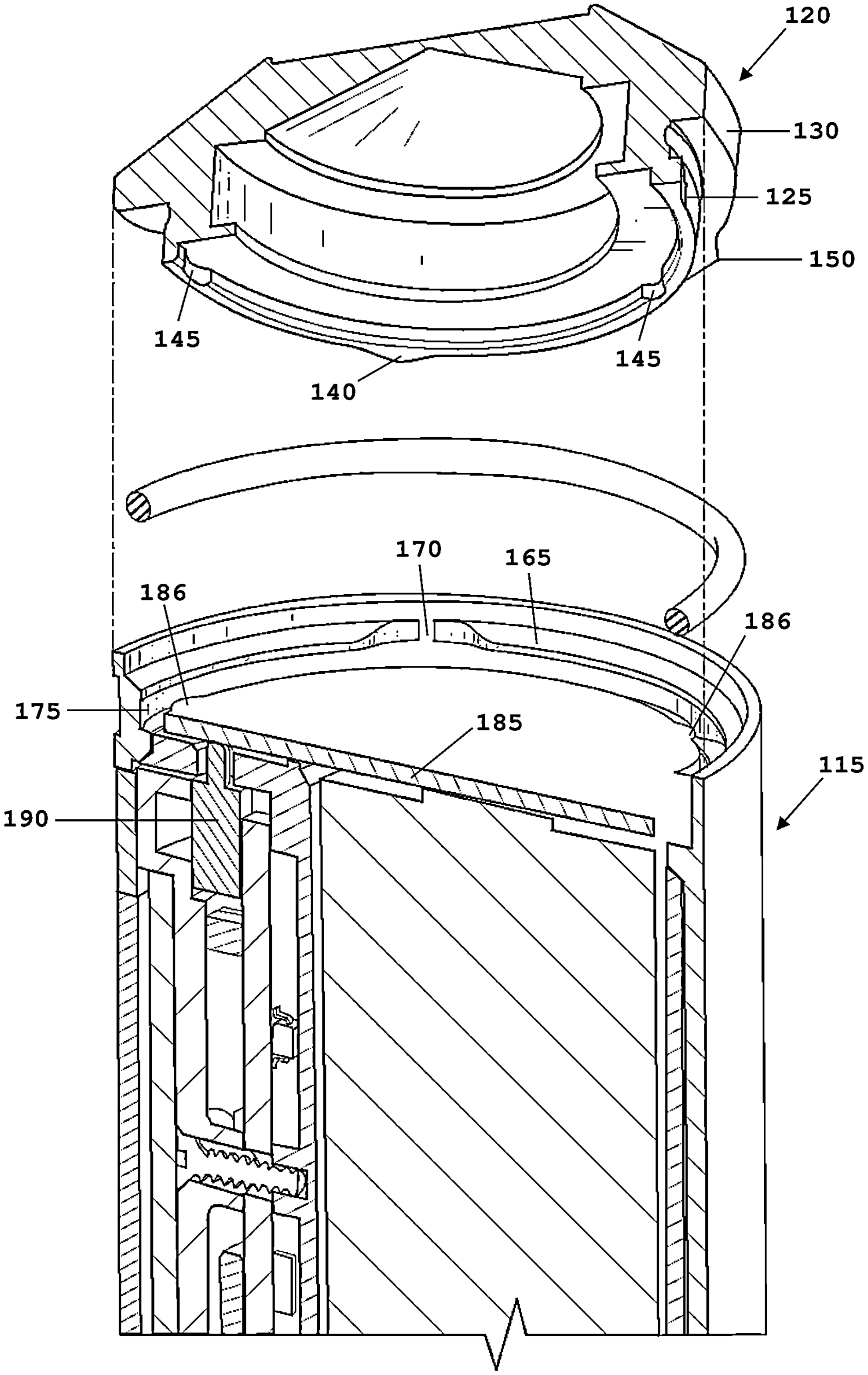
FIG. 6 is an exploded sagittal cross-sectional view of the distal end of the tattoo machine.

FIGS. 5 and 6 illustrate an electrical contact 190 according to an embodiment of the tattoo machine. The electrical contact 190 may be housed within a distal portion of the interior of the battery housing 115. The electrical contact 190 may be in electrical communication with a controller housed within an interior of the battery housing 115. The controller may act as an interface and be in electrical communication with the display, buttons, battery, and motor. The controller may be a printed circuit board with a processor and a memory storing computer instructions executed by the processor to perform the various functions of the tattoo machine. The electrical contact 190 may be made out of an electrically conductive metal. For example, the electrical contact 190 may be made of gold or copper or may be gold or copper-plated. The electrical contact 190 may be a pogo pin or other biased protrusion arranged to retractably extend in a direction, such as towards the cap 120. The electrical contact 190 has a tip and a body that are integrally formed one another. The body of the electrical contact 190 may be in electrical communication with the controller and housed within the distal portion of the interior of the battery housing 115 beneath the back wall of the interior space at the distal end of the battery housing 115. The tip of the electrical contact 190 may protrude into the interior space at the distal end of the battery housing 115 through a hole in the back wall of the interior space. This allows the tip of the electrical contact 190 to make contact with the contact plate 185 when the locking cap 130 is placed within the interior space at the distal end of the battery housing 115.

Modes of Operation

In some embodiments, rotating the locking cap 120 in a first or clockwise direction may turn on the tattoo machine 100. In the same embodiment, rotating the locking cap 120 in a second or counter-clockwise may turn off the tattoo machine 100.

Figure 7:
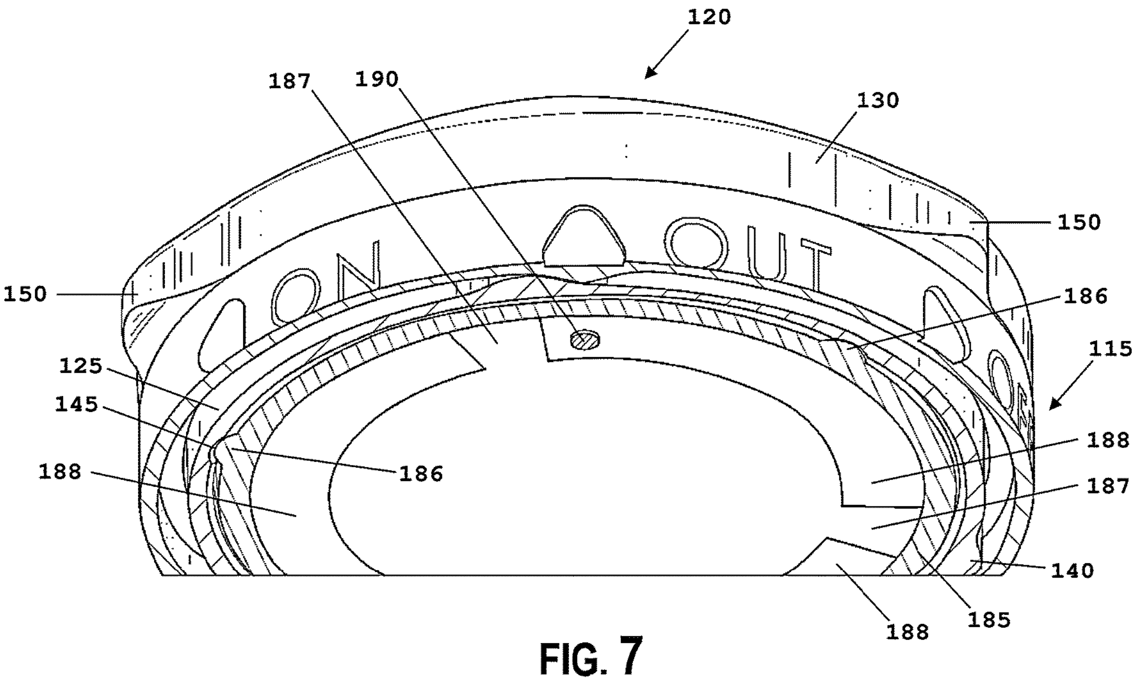
FIG. 7 is a traverse cross-sectional view of the distal end of the tattoo machine when the locking cap is rotated to the "OFF" position.

FIG. 7 illustrates the orientation of the locking cap 120, contact plate 185, battery housing 115, and the electrical contact 190 when the locking cap 120 is rotated counter-clockwise to the "OFF" position. When the locking cap 120 is rotated counter-clockwise to the "OFF" position, the electrical contact 190 makes contact with the non-contact area 188 of the contact plate 185. When the electrical contact 190 makes contact with the non-contact area 188 of the contact plate 185, the tattoo machine maintains the battery and motor in an electrical disconnected state, preventing the battery from delivering power to the motor. When the locking cap 120 is rotating counter-clockwise into the "OFF" position, the tabs 140 on the exterior radial surface of the proximal first ring 125 rotate within the channel 175 within the interior space at the distal end of battery housing 115 and abut against stops 180.

Figure 8:
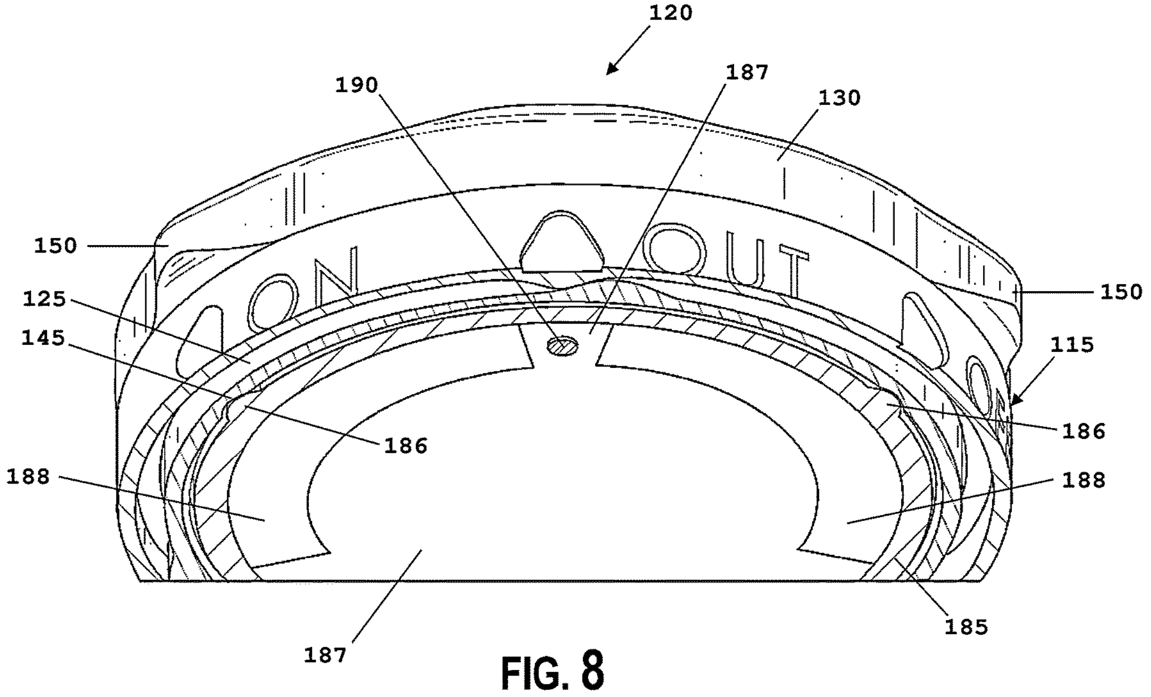
FIG. 8 is a traverse cross-sectional view of the distal end of the tattoo machine when the locking cap is rotated to the "ON" position.

FIG. 8 illustrates the orientation of the locking cap 120, contact plate 185, battery housing 115, and the electrical contact 190 as the locking cap 120 is rotated clockwise to the "ON" position. When the locking cap 120 is rotated clockwise to the "ON" position, the electrical contact 190 makes contact with the contact area 187 of the contact plate 185. When the electrical contact 190 makes contact with the contact area 187 of the contact plate 185, the electrical circuit connecting the battery to the motor is completed and power is delivered to the motor turning on the tattoo machine. When the locking cap 120 is rotating counter-clockwise into the "ON" position, the tabs 140 on the exterior radial surface of the proximal first ring 125 rotate within the channel 175 within the interior space at the distal end of battery housing 115 and abut against stops 180.

In an embodiment, the locking cap 120 can be removed from the distal end of battery housing 115 when the locking cap 120 is rotated to the "OUT" position as indicated by the etchings on the exterior surface of battery housing 115. In the "OUT" position, tabs 140 on the exterior radial surface of the proximal first ring 125 of the locking cap 120 may be aligned with the notches 170 on the circumferential lip 165 inside the interior space at the distal end of the battery housing 115. When the locking cap 120 is in the "OUT" position, the locking cap 120 may be dislodged from the distal end of the battery housing 115 by pulling upward on the locking cap 120, thus giving access to the interior space at the distal end of the battery housing 115 for disassembling the tattoo machine 100, troubleshooting the tattoo machine 100, or swapping the battery.

The illustrations of arrangements described herein are intended to provide a general understanding of the structure of various embodiments, and they are not intended to serve as a complete description of all the elements and features of apparatus and systems that might make use of the structures described herein. Other arrangements may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Thus, although specific arrangements have been illustrated and described herein, it should be appreciated that any arrangement calculated to achieve the same purpose may be substituted for the specific arrangement shown. This disclosure is intended to cover any and all adaptations or variations of various embodiments and arrangements of the invention. Combinations of the above arrangements, and other arrangements not specifically described herein, will be apparent to those of skill in the art upon reviewing the above description. Therefore, it is intended that the disclosure not be limited to the particular arrangement(s) disclosed as the best mode contemplated for carrying out this invention, but that the invention will include all embodiments and arrangements falling within the scope of the appended claims.

The foregoing is provided for purposes of illustrating, explaining, and describing embodiments of this invention. Modifications and adaptations to these embodiments will be apparent to those skilled in the art and may be made without departing from the scope or spirit of this invention. Upon reviewing the aforementioned embodiments, it would be evident to an artisan with ordinary skill in the art that said embodiments can be modified, reduced, or enhanced without departing from the scope and spirit of the claims described below. Although some of the drawings illustrate a number of operations/steps in a particular order, operations which are not order-dependent may be reordered and other operations may be combined or broken out. While some reordering or other groupings are specifically mentioned, others will be apparent to those of ordinary skill in the art and so do not present an exhaustive list of alternatives.

The invention claimed is:

1. A tattoo machine, comprising:

a tattoo machine housing, wherein the tattoo machine housing comprises:

a grip section that houses a motor;

a battery housing that houses a battery that powers the motor, the battery housing section having a detachable locking cap, wherein the battery housing section defines a battery housing longitudinal axis and detachably couples with the locking cap;

a contact plate with a plurality of protrusions that extend radially relative to the battery housing longitudinal axis;

an electrical contact that engages the contact plate to electrically connect the battery to power the tattoo machine;

wherein the tattoo machine is turned on by rotating the locking cap in a first direction;

wherein the tattoo machine is turned off by rotating the locking cap in a second direction; and wherein the second direction is opposite the first direction.

2. The tattoo machine of claim 1, wherein the locking cap further comprises a proximal first ring, a middle second ring, and a distal convex portion, wherein the proximal first ring is fixedly attached to a proximal side of the middle second ring, wherein the middle second ring is fixedly attached to a proximal side of the distal convex portion.

3. The tattoo machine of claim 2, wherein an outer diameter of the middle second ring is larger than an outer diameter of the proximal first ring.

4. The tattoo machine of claim 2, wherein the distal convex portion includes recesses and a flat surface located on a distal side of the distal convex portion.

5. The tattoo machine of claim 2, wherein the distal end of the battery housing section further includes an interior space for receiving the proximal first ring of the locking cap.

6. The tattoo machine of claim 5, wherein the proximal first ring includes tabs on an exterior radial surface, wherein the tabs are received by notches in the interior space on the distal end of the battery housing section, wherein the locking cap is secured to the battery housing section by placing the tabs of the proximal first ring within the notches on the distal end of the battery housing section and rotating the locking cap in either a clockwise or counterclockwise direction.

7. The tattoo machine of claim 6, wherein the interior space further includes stops located a distance from the notches, wherein the tabs abut against the stops when the locking cap is rotated in either direction.

8. The tattoo machine of claim 1, wherein the plurality of protrusions are located on a peripheral edge of the contact plate.

9. The tattoo machine of claim 8, wherein the plurality of protrusions engage with indentations located on an inner circumferential edge of a interior space on the proximal end of the locking cap to detachably secure the contact plate to the locking cap.

10. The tattoo machine of claim 1, wherein the contact plate includes contact areas and non-contact areas.

11. The tattoo machine of claim 10, wherein the electrical contact makes contact with the contact area of the contact plate when the locking cap is rotated in a first direction.

12. The tattoo machine of claim 11, wherein power is generated between the battery and the motor when the electrical contact makes contact with the contact area of the contact plate.

13. The tattoo machine of claim 10, wherein the electrical contact makes contact with the non-contact area of the contact plate when the locking cap is rotated in a second direction.

14. The tattoo machine of claim 13, wherein the battery and the motor are maintained in an electrically disconnected state when the electrical contact makes contact with the non-contact area of the contact plate.

15. The tattoo machine of claim 10, wherein the contact areas and non-contact areas are oriented with respect to the protrusions such that the contact plate can be placed within the locking cap in any configuration.

16. The tattoo machine of claim 10, wherein the contact areas are made of copper and the non-contact areas are made of nonconducting material.

17. The tattoo machine of claim 1, wherein an exterior surface of the locking cap is rubberized to provide grip to a user when turning the locking cap.

18. The tattoo machine of claim 1, wherein the locking cap is made out of plastic, metal, rubber or a combination thereof.

19. The tattoo machine of claim 18, wherein the locking cap is machined from a sheet or block of metal using a mill, lathe, or water jet cutting machine.

* * * * *